United States Patent [19]

Kim et al.

[11] Patent Number: 4,978,797
[45] Date of Patent: Dec. 18, 1990

[54] PROCESS FOR THE PREPARATION OF 2-HYDROXY-4-(HYDROXYALKOXY)-BENZOPHENONE

[75] Inventors: Bongsub Kim, Grosse Ile, Mich.; Hermann Kaack, Ruppertsberg, Fed. Rep. of Germany

[73] Assignee: BASF Corporation, Parsippany, N.J.

[21] Appl. No.: 439,722

[22] Filed: Nov. 21, 1989

[51] Int. Cl.$^5$ .............................................. C07C 45/71
[52] U.S. Cl. .................................................. 568/315
[58] Field of Search ........................ 568/375, 315, 608

[56] References Cited

U.S. PATENT DOCUMENTS

| | | | |
|---|---|---|---|
| 3,617,599 | 10/1972 | Dalbey ................................. | 568/315 |
| 3,676,471 | 7/1972 | Eggenspagen et al. ............. | 560/315 |
| 3,923,901 | 12/1975 | Battin et al. ........................ | 568/315 |
| 4,261,922 | 4/1981 | Kem ................................... | 568/315 |
| 4,885,396 | 12/1989 | Hahn et al. ......................... | 568/315 |

FOREIGN PATENT DOCUMENTS

| | | | |
|---|---|---|---|
| 44-8656 | 4/1969 | Japan ................................. | 568/315 |
| 61-200941 | 9/1986 | Japan ................................. | 568/315 |

*Primary Examiner*—James H. Reamer
*Attorney, Agent, or Firm*—William G. Conger; Martin P. Connaughton

[57] ABSTRACT

The present invention relates to an improved process for the preparation of 2-hydroxy-4-(hydroxyalkoxy)-benzophenone. More particularly the invention is directed to the oxyalkylation of 2,4-dihydroxy benzophenone, using $C_2$ to $C_4$ alkylene oxides in the presence of a basic catalyst and water. Such products are useful as ultraviolet light absorbers.

7 Claims, No Drawings

PROCESS FOR THE PREPARATION OF 2-HYDROXY-4-(HYDROXYALKOXY)-BENZOPHENONE

BACKGROUND OF THE INVENTION

The present invention relates to a process for the preparation of 2-hydroxy-4-(hydroxyalkoxy)-benzophenone. More particularly the present invention is concerned with a method for oxyalkylating 2,4-dihydroxybenzophenone in the presence of water using a basic catalyst.

It is well known that compounds such as those produced by the process of Applicant's present invention may be used as ultraviolet light absorbers and are particularly useful as light-stabilizers in resinous compositions.

Various synthesis schemes for making the subject compound have been disclosed in the literature. Applicant's co-pending U.S. Pat. application, No. 197,042, now U.S. Pat. No. 4,885,396, discloses a method of preparing the subject compound, wherein the 2,4dihydroxybenzophenone is reacted with ethylene carbonate in the presence of a quaternary ammonium salt catalyst, at temperatures preferably between 140° C. to about 175° C. The reaction may also be carried out in an organic solvent which is inert to the reactants but it is preferably carried out in the absence of any solvent.

Eggensperger discloses in U.S. Pat. No. 3,676,471 a method of preparing 2-hydroxy-4-(hydroxyethoxy)benzophenone by reacting the dihydroxybenzophenone with ethylene carbonate or ethylene oxide in an organic solvent, in the presence of a basic catalyst preferably alkali carbonates, alkaline earth carbonates, or alkali alcoholates. This method has a number of disadvantages. It requires the use of solvents, particularly ketones. Because of the basic nature of the reaction mixture only substantially inert ketones may be employed. Further, Example 1 discloses that the reaction product is obtained by extraction with a chlorinated hydrocarbon. Halogenated hydrocarbons present problems because they are toxic and potential environmental hazards.

SUMMARY OF THE INVENTION

This invention comprises an improved process for the oxyalkylation of dihydroxybenzophenones providing high yields at reduced reaction temperatures without the use of organic solvents. In particular the invention comprises the use of basic catalysts, such as potassium hydroxide, as the oxyalkylation catalyst for the reaction of a dihydroxybenzophenone with a $C_2$ to $C_4$ alkylene oxide. The reaction is carried out in the presence of water. The process generates product in high yield and purity. The product is particularly useful as an ultraviolet light stabilizer in resinous compositions.

DETAILED DESCRIPTION OF THE INVENTION

A manufacturing procedure has been developed whereby a 2,4-dihydroxybenzophenone is oxyalkylated in the presence of at least 0.1 weight percent water based on the weight of the 2,4-dihydroxybenzophenone water, using basic catalysis.

The 2,4-dihydroxy compounds used as starting materials are well known, or are able to be prepared in a conventional fashion, e.g. by the Friedel-Crafts-Acylation of resorcinol with carboxylic acid chlorides, preferably benzoyl chloride. The $C_2$ to $C_4$ oxyalkylating agents are ethylene oxide, propylene oxide, or butylene oxide, preferably ethylene oxide. The basic catalyst used is an alkali metal hydroxide, preferably potassium hydroxide. Commercially prepared aqueous solutions, e.g. 45% KOH, may be used.

In carrying out the process of the present invention, the 2,4-dihydroxybenzophenone, the catalyst, preferably KOH, and distilled water are added with stirring to a reaction vessel. The amount of catalyst used is not critical, amounts greater than about 0.1 weight percent based on the weight of the dihydroxybenzophenone may be used. However, it is preferred that the amount of catalyst used is between about 0.5 weight percent and 1.5 weight percent, and most preferably between about 0.7 weight percent and about 1.1 weight percent. The process may be carried out without the addition of the distilled water, however at least 0.1 weight percent water should be present and it is preferred that there be at least 7 weight percent present based on the weight of the dihydroxybenzophenone.

The vessel is sealed and padded with an inert gas, preferrably nitrogen. The temperature is slowly raised to between about 100° C. to about 145° C, preferably between about 100° C. to about 125° C, and most preferably between 105° C. to about 110° C.

The reaction vessel is pressurized with an inert gas and the $C_2$ to $C_4$ alkylene oxide is added at a rate such that the pressure in the reaction vessel does not exceed 90 psig. The alkylene oxide is preferably in about a 1:1 molar ratio with the diydroxybenzophenone. However, this synthesis is not limited to a 1 mole adduct of a $C_2$ to $C_4$ alkylene oxide and a dihydroxybenzophenone. Alkylene oxide adducts of greater than 1 mole are considered to be within the scope of the invention. After addition of the oxide is completed the reaction mixture is allowed to react out to constant pressure. At this point the mixture may be subjected to stripping to remove volatiles, however it is not mandatory. If necessary the mixture is cooled to about 105° C. It is then vented to 0 psig with the inert gas and the product discharged. The product, a 2-hydroxy-4-(hydroxyalkoxy)-benzophenone may easily be recovered from the reaction mixture, some possible methods being purification in aqueous media or recrystallization in organic solvent/water medium, filtration, and drying.

Having described the invention, the following examples are given merely as illustrative of the present invention and are not to be considered as limiting.

EXAMPLE 1

To a prepared one gallon autoclave, 1000 g of 2,4-dihydroxybenzophenone (4.5 mole, 2.9 percent $H_2O$) 16.2 g of 45 % KOH and 70.3 g of distilled water were added. The autoclave was then sealed, purged, and pressure checked. The reactor was heated slowly to 105° C. to 110° C. under 2 to 3 psig nitrogen while allowing the 2,4-dihydroxybenzophenone to melt. The autoclave was pressurized to 34 psig with nitrogen with agitation, and 210 g of ethylene oxide (4.77 mole) were added at 150 to 175 g/hour and <90 psig. The reaction mixture was reacted out to constant pressure and then evacuated slowly to 70 mmHg to strip low volatiles. The autoclave was vented to 0 psig with nitrogen and the product was discharged. 15.7 g of the molten reaction mixture were stirred with about 200 g of water. The solidified product was filtered off and the wet product cake were dried under vacuum. 14.6 g of light tan colored product was recovered in a yield of 99 percent, having a melting point of 91.5 to 97.5° C.

Analysis: 98.9 percent 2-hydroxy-4-($\beta$-hydroxyethoxy)-benzophenone, 1.0 percent 2,4-dihydroxybenzophenone.

EXAMPLE 2

To a prepared one gallon autoclave, 1000 g of 2,4dihydroxybenzophenone (4.6 moles, purity 99.4 percent), 20 g of 45 % KOH (0.16 mole) were added. The autoclave was then sealed, purged, and pressure checked. The reactor was heated to 140° C. under 3 psig nitrogen allowing the 2,4dihydroxybenzophenone to melt. 283 g of propylene oxide (4.93 mole) were added at 125 to 150 g/hour and <90 psig. The mixture was reacted out to constant pressure. After cooling to 100° C. and venting to 0 psig with nitrogen, the product was discharged. 5.5 g of the crude product were crystallized in methanol/water and yielded 3.5 g of a yellow solid compound having a melting point of 78 to 80° C.

Yield 66 percent of the theoretical.

What is claimed is:

1. A process for the preparation of a 2-hydroxy4-(hydroxyalkoxy)-benzophenone, comprising reacting under an inert gas a 2,4-dihydroxybenzophenone with a $C_2$ to $C_4$ alkylene oxide in the presence of from about 0.1 weight percent to about 1.5 percent of a basic catalyst, and at least 0.1 weight percent water, at temperatures between about 100° C. to about 145° C, wherein the weight percentages are based on the weight of the 2,4-dihydroxybenzophenone.

2. A process as claimed in claim 1 wherein said alkylene oxide is ethylene oxide.

3. A process as claimed in claim 1 wherein said basic catalyst is an alkali metal hydroxide and constitutes from about 0.5 weight percent to about 1.5 weight percent based on the weight of the 2,4-dihydroxybenzophenone.

4. A process as claimed in claim 1 wherein said water is used as a solvent and constitutes at least 7 weight percent based on the weight of the 2,4-dihydroxybenzophenone.

5. A process as claimed in claim 1 wherein said temperature is between about 105° C. to about 125° C.

6. A process as claimed in claim 1 wherein said basic catalyst is potassium hydroxide.

7. A process for the production of a 2-hydroxy-4($\beta$-hydroxyethyoxy)-benzophenone comprising:
    (a) reacting, under an inert gas, 2,4dihydroxybenzophenone with,
    (b) ethylene oxide in about a 1:1 molar ratio with the 2,4-dihydroxybenzophenone,
    (c) in the presence of about 0.7 weight percent KOH based on the weight of the 2,4-dihydroxybenzophenone,
    (d) in the presence of about 7 weight percent distilled water based on the weight of the 2,4-dihydroxybenzophenone,
    (e) at a reaction temperature of about 105° C. to about 110° C, and
    (f) recovering the 2-hydroxy-4-($\beta$-hydroxyethoxy)-benzophenone by purifying in an aqueous solution, filtering, and then vacuum drying the solid 2-hydroxy-4-($\beta$-hydroxyethoxy)benzophenone.

* * * * *